(12) United States Patent
Horiuchi et al.

(10) Patent No.: US 7,751,524 B2
(45) Date of Patent: Jul. 6, 2010

(54) X-RAY COMPUTED TOMOGRAPHY APPARATUS

(75) Inventors: Tetsuya Horiuchi, Tsurugashima (JP); Satoru Nakanishi, Utsunomiya (JP); Naruomi Akino, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 168 days.

(21) Appl. No.: 12/179,918

(22) Filed: Jul. 25, 2008

(65) Prior Publication Data

US 2009/0028288 A1    Jan. 29, 2009

(30) Foreign Application Priority Data

Jul. 25, 2007    (JP)    .............................. 2007-193690

(51) Int. Cl.
*A61B 6/00*    (2006.01)

(52) U.S. Cl. .............................................. 378/4; 378/8

(58) Field of Classification Search .................... 378/4, 378/8

See application file for complete search history.

(56) References Cited

U.S. PATENT DOCUMENTS

| | | | | |
|---|---|---|---|---|
| 5,999,587 A | * | 12/1999 | Ning et al. | 378/4 |
| 6,504,892 B1 | * | 1/2003 | Ning | 378/4 |
| 6,907,100 B2 | * | 6/2005 | Taguchi | 378/4 |
| 7,298,813 B2 | | 11/2007 | Tsuyuki et al. | |
| 2005/0152494 A1 | * | 7/2005 | Katsevich | 378/62 |

* cited by examiner

*Primary Examiner*—Edward J Glick
*Assistant Examiner*—Alexandeer H Taningco
(74) *Attorney, Agent, or Firm*—Oblon, Spivak, McClelland, Maier & Neustadt, L.L.P.

(57) ABSTRACT

An X-ray computed tomography apparatus includes a gantry, a reconstruction processing unit which generates first volume data on the basis of a projection data set which covers an angle range of 180°+a fan angle and also generates second volume data on the basis of a projection data set which covers an angle range of 360°, a correction data generating unit which generates correction data for reducing a cone beam artifact on the basis of a difference between the first volume data and the second volume data, and a correction unit which corrects the first volume data on the basis of the correction data.

21 Claims, 8 Drawing Sheets

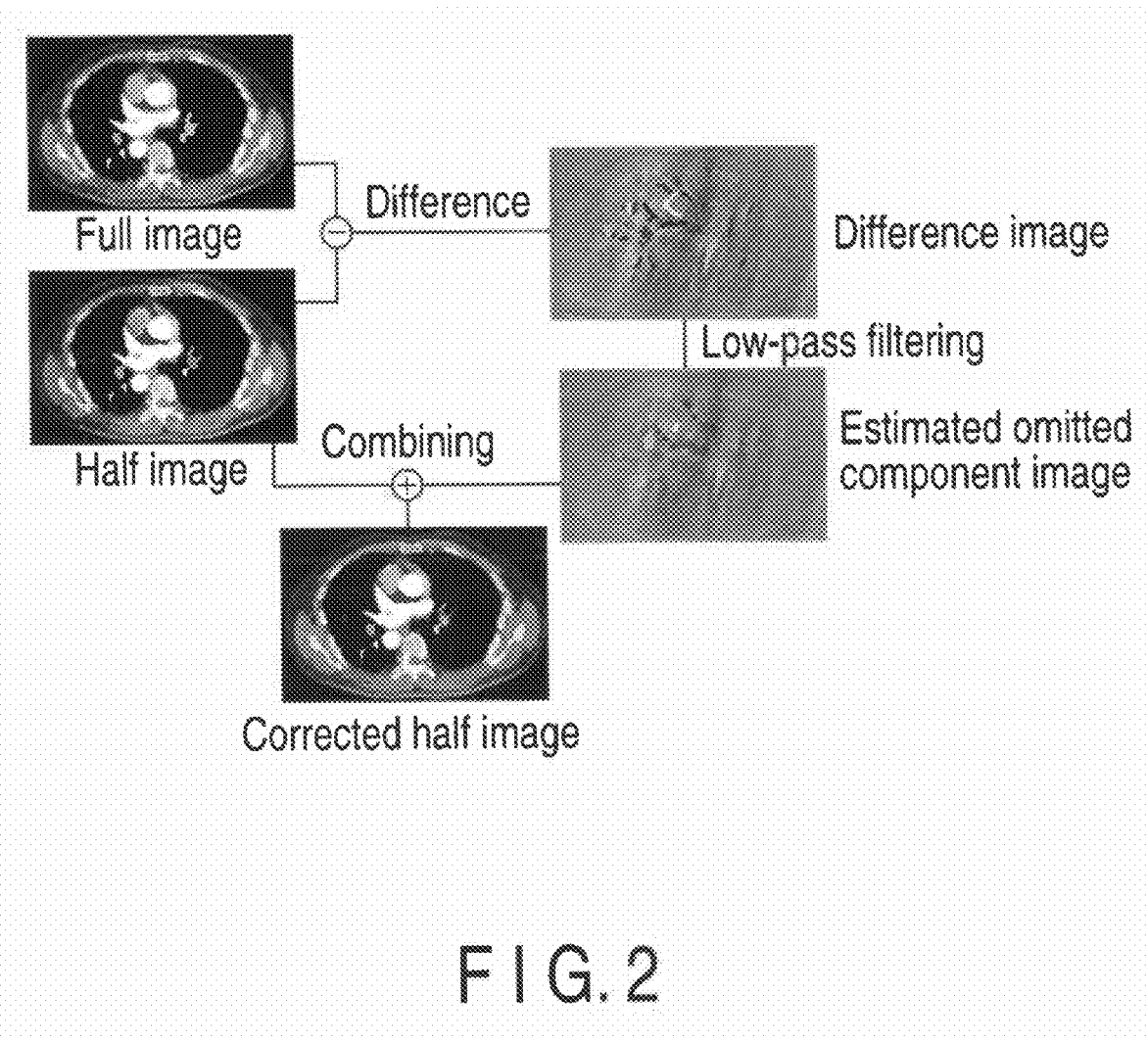
F I G. 2

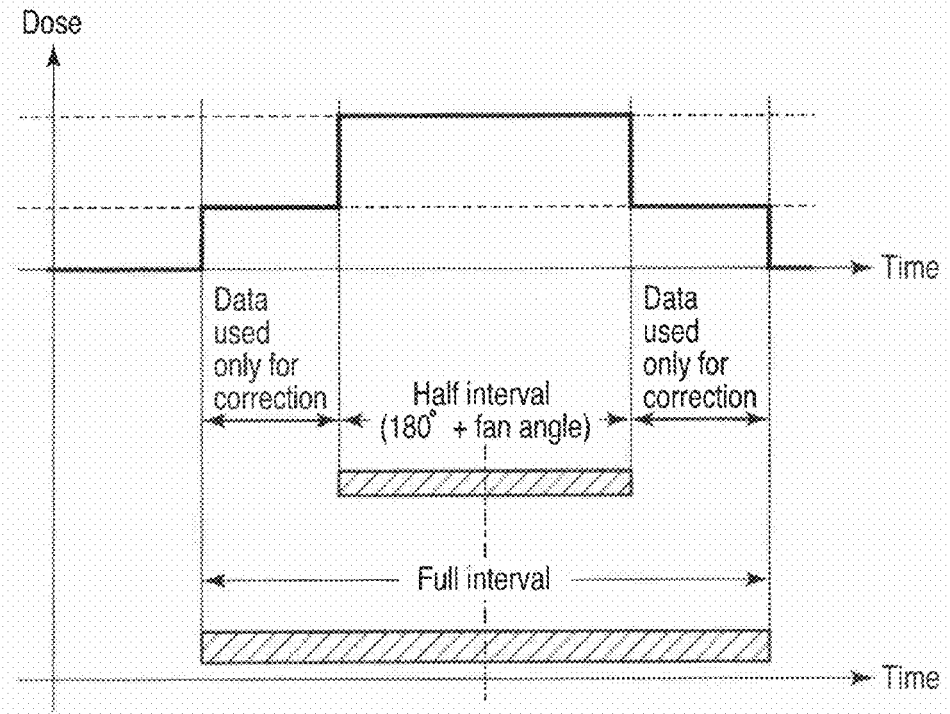
F I G. 3
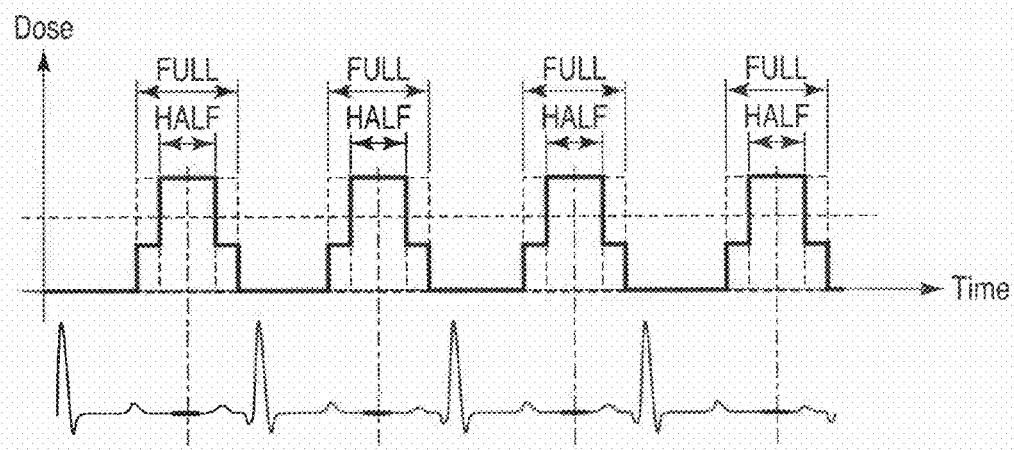
F I G. 4

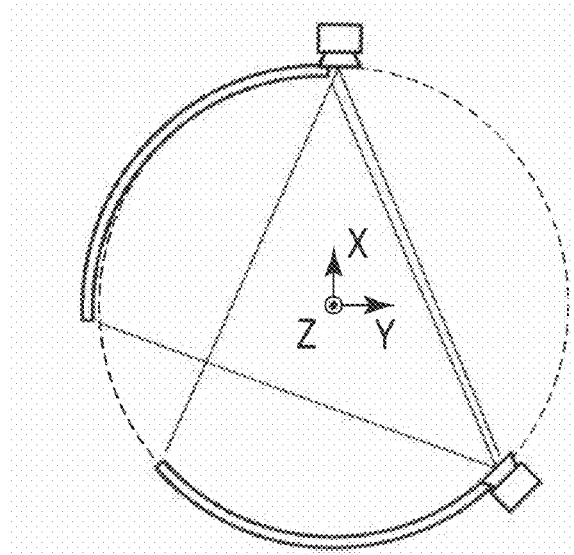
F I G. 10
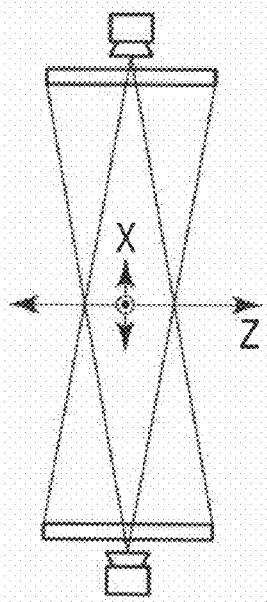
F I G. 11

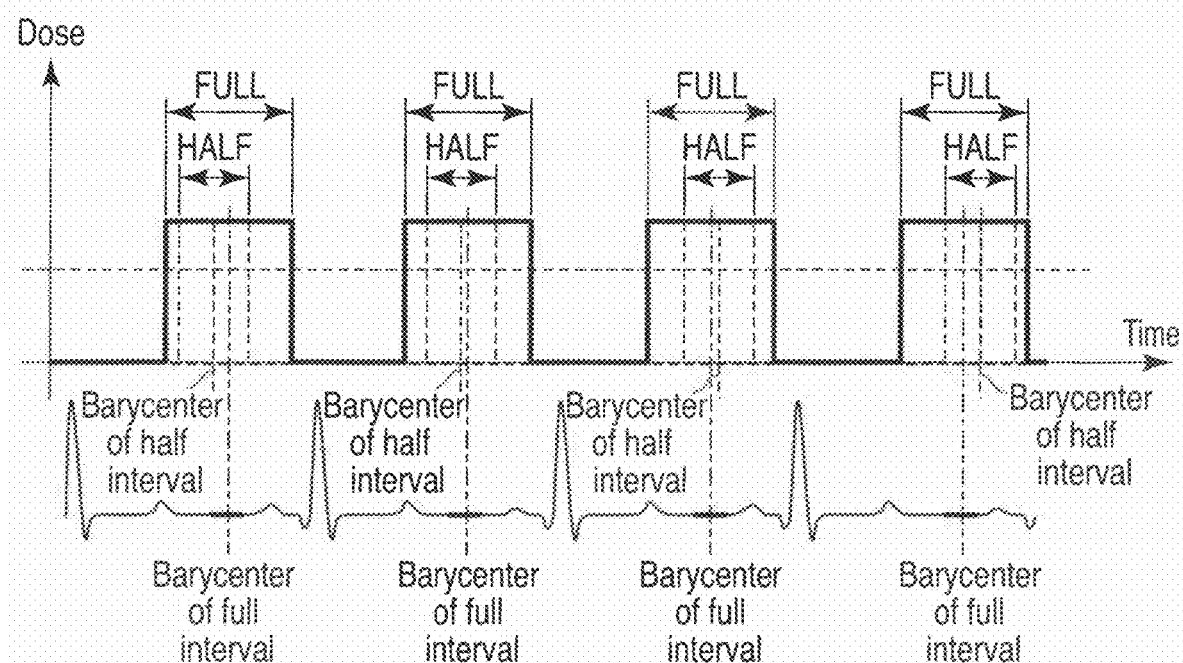
F I G. 12

X-RAY COMPUTED TOMOGRAPHY APPARATUS

CROSS-REFERENCE TO RELATED APPLICATIONS

This application is based upon and claims the benefit of priority from prior Japanese Patent Application No. 2007-193690, filed Jul. 25, 2007, the entire contents of which are incorporated herein by reference.

BACKGROUND OF THE INVENTION

1. Field of the Invention

The present invention relates to a cone beam artifact reduction method for a half reconstruction method or the like which is higher (shorter) in time resolution than full reconstruction in cone beam helical reconstruction and, more particularly, to an X-ray computed tomography apparatus which obtains in-vivo information as an image by applying X-rays to a living body.

2. Description of the Related Art

In cone beam CT, as is known, when circular orbit acquisition is executed, radon data necessary to obtain a complete solution cannot be acquired, and more cone beam artifacts appear with an increase in the distance from the central plane. Consider half reconstruction in cone beam circular orbit scanning. Half reconstruction is characterized by being shorter (better) in time resolution than full reconstruction. However, half reconstruction is implemented with a fan beam but is not implemented with a cone beam. As shown in FIG. 10, with a fan beam, since so-called counter data exist, it is possible to obtain a complete solution if there is (180°+fan angle) data (half reconstruction).

On the other hand, as shown in FIG. 11, in cone beam CT, counter data do not pass through the same path except on the central plane due to the influence of the cone angle. This leads to the omission of radon data. Consequently, more noticeable cone beam artifacts appear than in full reconstruction, resulting in a deterioration in image quality.

As described above, in half reconstruction in cone beam reconstruction, the problem of cone beam artifacts is more noticeable. As a conventional technique, there has been proposed a technique of balancing a time resolution and artifacts by, for example, assigning a weight to one-rotation data instead of half-rotation data. However, such a technique is not a fundamental measure against "the omission of radon data", and is a technique which can at best change the manner of how artifacts are seen. That is, a fundamental solution has not been achieved.

Recently, the Line+Circle method has been proposed by Katsevich, the University of Central Florida. This technique is designed to obtain a complete solution by adding line data to half scanning. A prerequisite of this technique is that line data is in contact with the scan start or end point of half scanning. In the case of dynamic half reconstruction in dynamic scanning, this prerequisite does not hold. Obviously, this problem can be solved by acquiring many line data at each tube position. However, this technique is not practical in consideration of actual operation. In the case of segment reconstruction in which half-scanning data is obtained by using a plurality of heartbeat data obtained in ECG-gated reconstruction, a data group constituting half-scanning data sometimes exists discontinuously in the tube position direction. In such a case, the proposal by Katsevich cannot be used.

As described above, with regard to cone beam artifacts, the half reconstruction method is superior in time resolution at the sacrifice of image quality.

BRIEF SUMMARY OF THE INVENTION

It is an object of the present invention to suppress cone beam artifacts to the level of full reconstruction while maintaining the time resolution in half reconstruction.

According to an aspect of the present invention, there is provided an X-ray computed tomography apparatus comprising a gantry, a reconstruction processing unit which generates first volume data on the basis of a projection data set which covers an angle range of 180°+a fan angle and also generates second volume data on the basis of a projection data set which covers an angle range of 360°, a correction data generating unit which generates correction data for reducing a cone beam artifact on the basis of a difference between the first volume data and the second volume data, and a correction unit which corrects the first volume data on the basis of the correction data.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a view showing an outline of an image processing procedure in this embodiment;

FIG. 3 is a graph for explaining half reconstruction and full reconstruction in this embodiment;

FIG. 4 is a view showing an application to ECG-gated reconstruction in this embodiment;

FIG. 10 is a view showing counter paths in a fan;

FIG. 11 is a view showing the difference between counter paths in a cone; and

FIG. 12 is a graph showing another application to ECG-gated reconstruction in this embodiment.

DETAILED DESCRIPTION OF THE INVENTION

Figure 1:
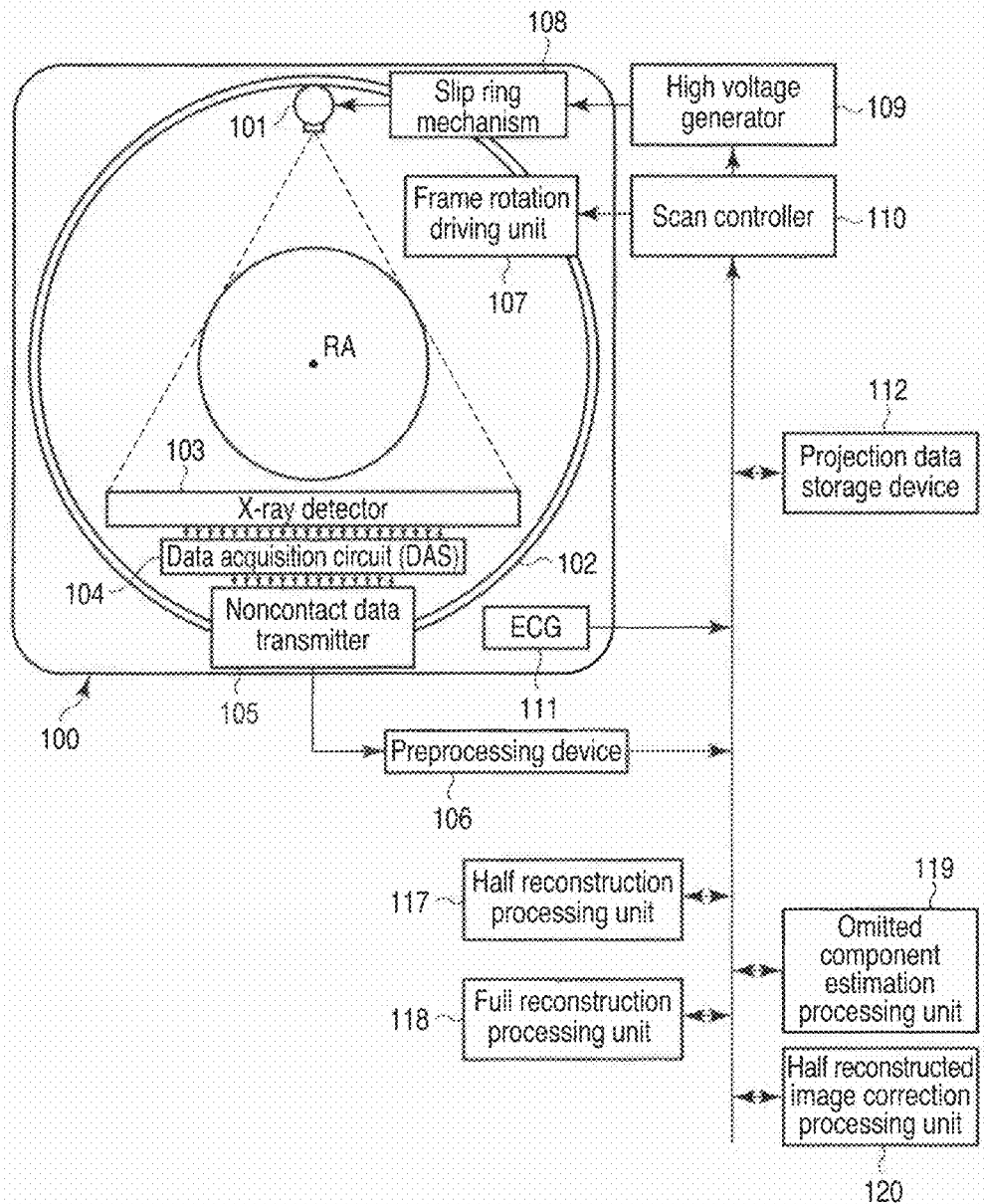
FIG. 1 is a block diagram showing the arrangement of an X-ray computed tomography apparatus according to an embodiment.

An embodiment of the present invention will be described below with reference to the views of the accompanying drawing. As shown in FIG. 1, a gantry 100 includes an X-ray tube device 101 which generates X-rays in a cone shape (cone beam). The X-ray tube device 101 generates X-rays upon receiving a tube voltage and a filament current from a high voltage generator 109 via a slip ring mechanism 108. The X-ray tube device 101 is mounted on a rotating frame 102, which is supported to be rotatable about a rotation axis RA, together with an X-ray detector 103. A frame rotation driving unit 107 is provided to rotate/drive the rotating frame 102.

The X-ray detector 103 faces the X-ray tube device 101 through the rotation axis RA. A cylindrical imaging area is provided centered on the rotation axis RA. An object is placed in the imaging area. An electrode of an electrocardiogram (ECG) 111 is attached to the object. The heartbeat data acquired by the electrocardiogram 111 during scanning is stored in a projection data storage unit 112 together with projection data.

The X-ray detector 103 detects the X-rays generated by the X-ray tube device 101 and transmitted through the object. The X-ray detector 103 is a multislice type or two-dimensional array type X-ray detector. That is, the X-ray detector 103 includes a plurality of X-ray detection element rows arranged in a line along the rotation axis RA. Each X-ray detection element row includes a plurality of X-ray detection elements arranged in a line along a direction perpendicular to the rotation axis RA.

A data acquisition circuit (DAS) 104 amplifies an output from the X-ray detector 103 for each channel and converts it into a digital signal. This data is sent to a preprocessing device 106 via a noncontact data transmitter 105. The preprocessing device 106 performs correction processing such as sensitivity correction for the data. A projection data storage device 112 then stores the resultant data as so-called projection data at a stage immediately before reconstruction processing.

A scan controller 110 controls the frame rotation driving unit 107, the high voltage generator 109, the data acquisition circuit 104, and the like to perform data acquisition (scanning).

For the sake of descriptive convenience, a half reconstruction processing unit 117 and a full reconstruction processing unit 118 which constitute a reconstruction apparatus will be described separately. The half reconstruction processing unit 117 applies a first data redundancy correction weight W1 to the projection data set (first projection data set) acquired while the X-ray tube device 101 moves in an angle range of (180°+fan angle) (first angle range), and reconstructs first volume data on the basis of the first projection data set to which the weight is applied. The full reconstruction processing unit 118 applies a second data redundancy correction weight W2 to the projection data set (second projection data set) acquired while the X-ray tube device 101 moves in an angle range (360°) (second angle range) wider than the first angle range, and reconstructs second volume data on the basis of the second projection data set to which the weight is applied.

An omitted component estimation processing unit 119 estimates the spatial distribution of an omitted component (omitted component image) due to "the omission of radon data" on the basis of the difference between the first volume data obtained by half reconstruction and the second volume data obtained by full reconstruction. As shown in FIG. 2, in practice, the omitted component estimation processing unit 119 generates a difference image containing an omitted component due to "radon data omission" by subtracting the first volume data obtained by half reconstruction and the second volume data obtained by full reconstruction from each other. An omitted component image is generated by removing high-frequency components due to a long time resolution essential to full reconstruction from the difference image by low-pass filtering.

As shown in FIG. 3, the center (barycenter) of an angle range of 360° (full interval) on which the second volume data obtained by full reconstruction is based preferably coincides with the center (barycenter) of an angle range of (180°+fan angle) (half interval) on which the first volume data obtained by half reconstruction is based. As shown in FIG. 4, this state is preferable for ECG-gated reconstruction.

In practice, as shown in FIG. 12, the barycenter of each half interval does not necessarily coincide with the barycenter of a corresponding full interval. This is because ECG gating during data acquisition includes a prediction element. For this reason, a full interval is set in a range including a desired cardiac phase, and the barycenter of a half interval is set at the desired cardiac phase at a stage before reconstruction processing after data acquisition by referring to an electrocardiogram measured at the time of data acquisition. In this case, to set a half interval at an arbitrary position in a full interval, data is acquired at a high dose throughout the entire full interval.

A half reconstructed image correction processing unit 120 corrects the first volume data obtained by half reconstruction on the basis of an omitted component image. More specifically, the omitted component image is added to the first volume data obtained by half reconstruction. This makes it possible to achieve image quality similar to that obtained by full reconstruction together with a short time resolution achieved by half reconstruction.

The procedure of processing in this embodiment will be described below. Note that all processing programs for the following plurality of processes are stored in the apparatus to allow the user to selectively use the processes.

Figure 5:
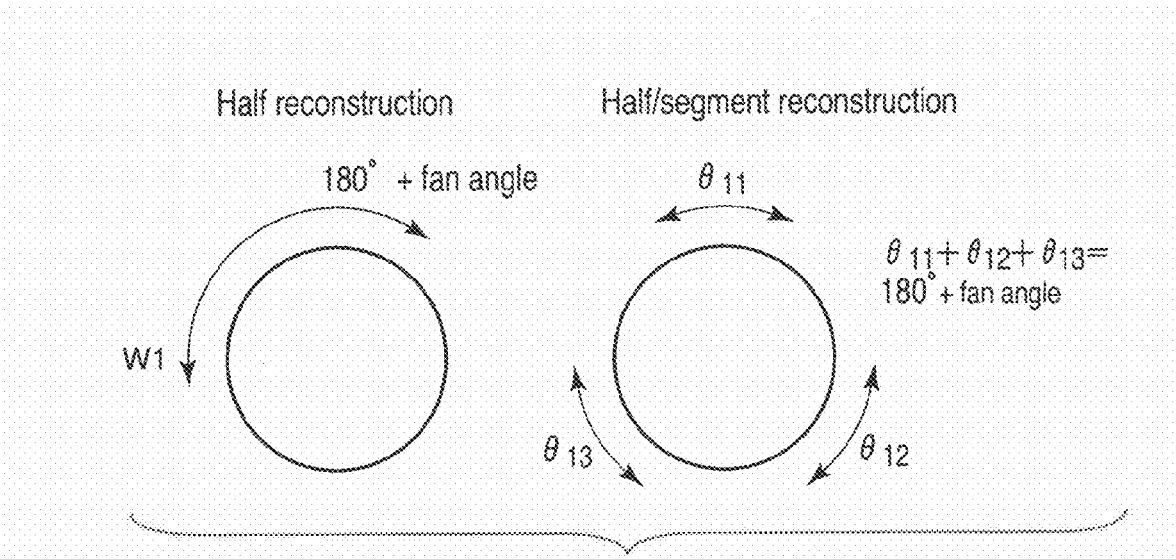
FIG. 5 is a view showing angle ranges in the use of half reconstruction applied to this embodiment and a combination with segment reconstruction.
Figure 6:
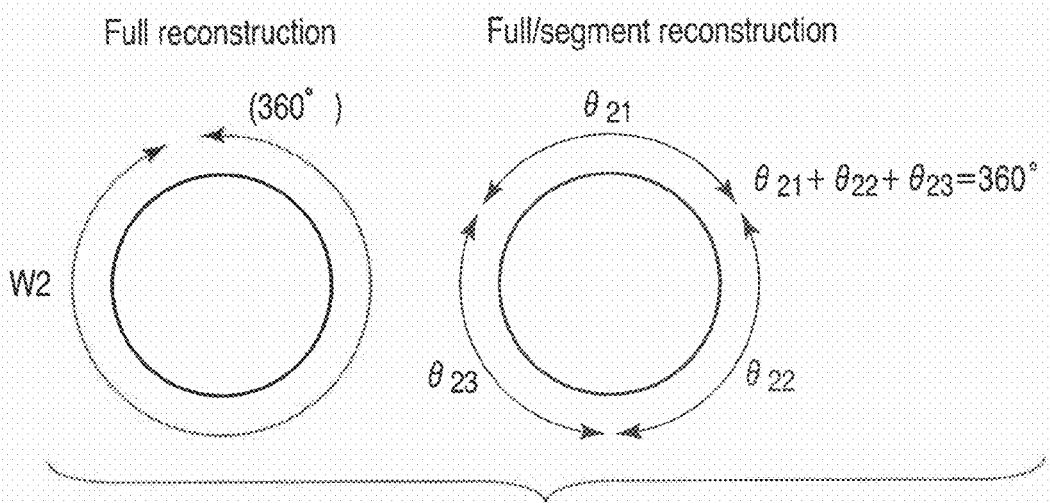
FIG. 6 is a view showing angle ranges in the use of full reconstruction applied to this embodiment and a combination with segment reconstruction.
Figure 7:
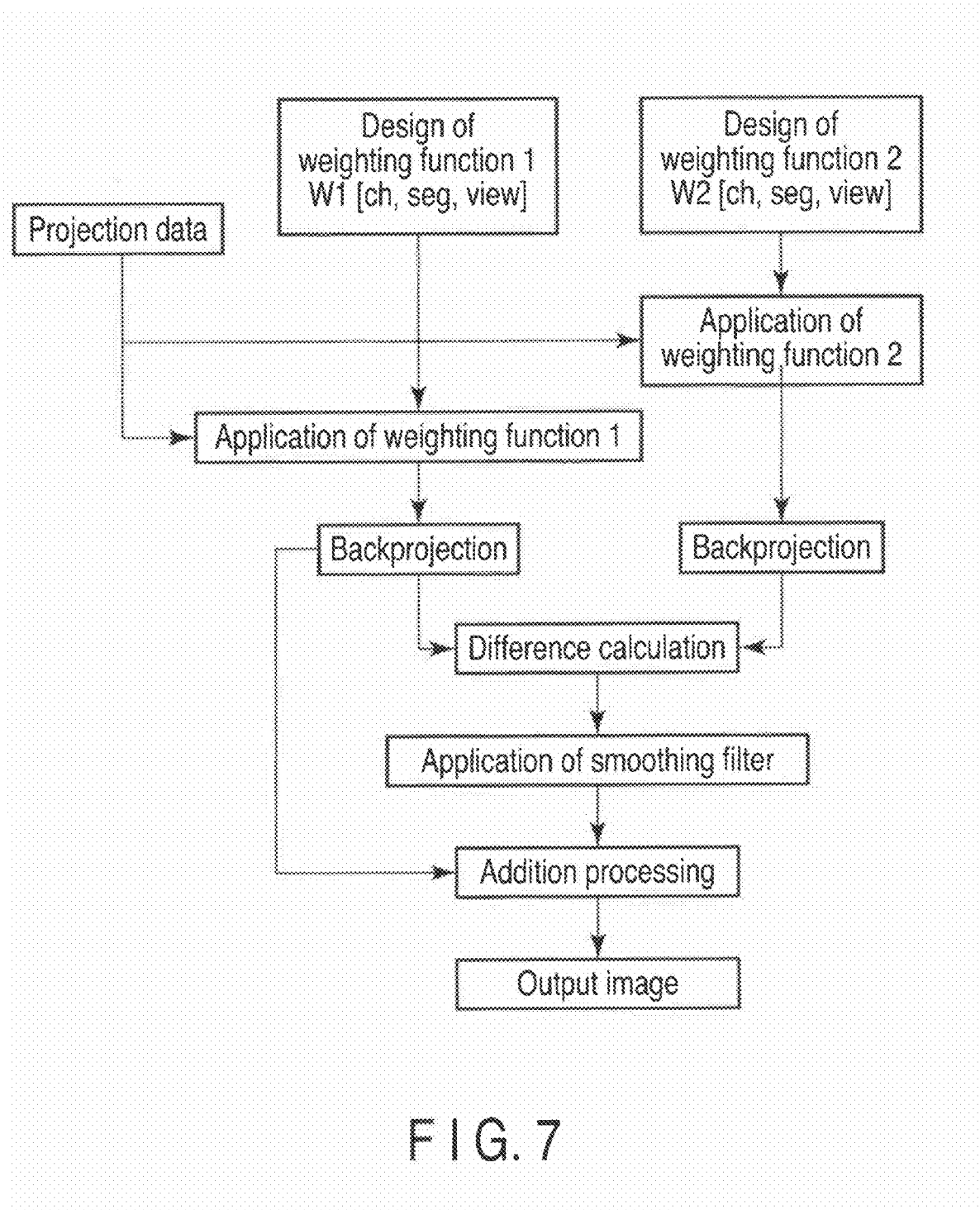
FIG. 7 is a flowchart showing a first image processing procedure in this embodiment.

As shown in FIG. 7, first of all, redundancy correction weighting functions W1[ch, seg, view] and W2[ch, seg, view] are designed. W1[ ] depends on the reconstruction method designated by the user and is the Parker weight when half reconstruction is designated. In the case of ECG-gated segment reconstruction shown in FIGS. 5 and 6, this weighting function takes a more complex form. W2[ ] is a weight corresponding to full reconstruction. In the case of one-rotation data, since data acquisition is performed twice in opposite directions with respect to each path, W2[ ]=0.5. Volume data (first volume data) is generated by applying the weighting function W1 to a projection data set corresponding to (180°+fan angle) and performing backprojection. In addition, volume data (second volume data) is generated by applying the weighting function W2 to a projection data set corresponding to (360°) and performing backprojection.

Difference volume data as the spatial distribution of the omitted component due to the omission of radon data is generated by subtracting the first and second volume data from each other. Unnecessary high-frequency components due to the low (long) time resolution of full reconstruction are removed by applying smoothing to the difference volume data. Smoothing is processing within an axial plane. Finally, corrected first volume data is obtained by adding the omitted component image (difference volume data) having undergone smoothing to the first volume data reconstructed by using the weighting function W1.

Figure 8:
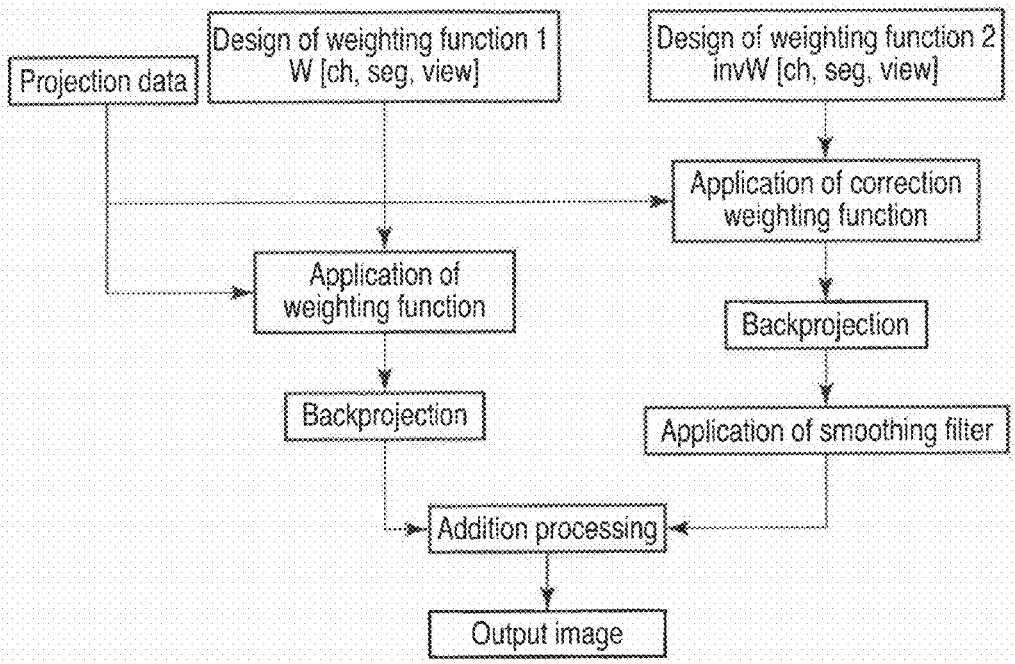
FIG. 8 is a flowchart showing a second image processing procedure in this embodiment.

It suffices to follow the procedure of processing shown in FIG. 8. First of all, the weighting function W[ch, seg, view] depends on the reconstruction method designated by the user and is, for example, the Parker weight when half reconstruction is designated (as in the case of W1 in the above procedure). In the case of ECG-gated segment reconstruction, this weighting function takes a more complex form.

A correction weighting function invW[ch, view] is basically defined by the following equation. The correction weighting function invW[ch, view] is generated to complete the difference processing in FIG. 7 in a projection data area.

$$invW[ch,seg,view]=wFULL[ch,seg,view]-W[ch,seg,view]$$

When input data is one-rotation data, a full reconstruction weighting function wFull[ch, seg, view] becomes "0.5". Assume that input data is data corresponding to more than one rotation. In this case, when the data are added with reference to the tube position and accumulated into data corresponding to one rotation, wFull[ch, seg, view] needs to be designed to become "0.5". This operation corresponds to that in segment reconstruction or the like, and a weighting function is designed to "construct full-rotation data which are discontinuous data and exist from any tube positions as a total".

An image (first volume data) is obtained by applying the weighting function W[ch, seg, view] to a projection data set obtained by half reconstruction and performing backprojection. An image (volume data) is obtained by applying the correction weighting function invW[ch, seg, view] to a projection data set obtained by full reconstruction and performing backprojection.

Smoothing is applied to the image (volume data) to which the correction weighting function has been applied. This is processing within an axial plane. Finally, the first volume data is corrected by adding the two images (volume data). The addition method used in this case is the one considering a cone angle. When the cone angle is zero, the weight of a correction image is set to zero. As the absolute value of the cone angle increases, the contribution ratio of the correction image is designed to be increased.

Figure 9:
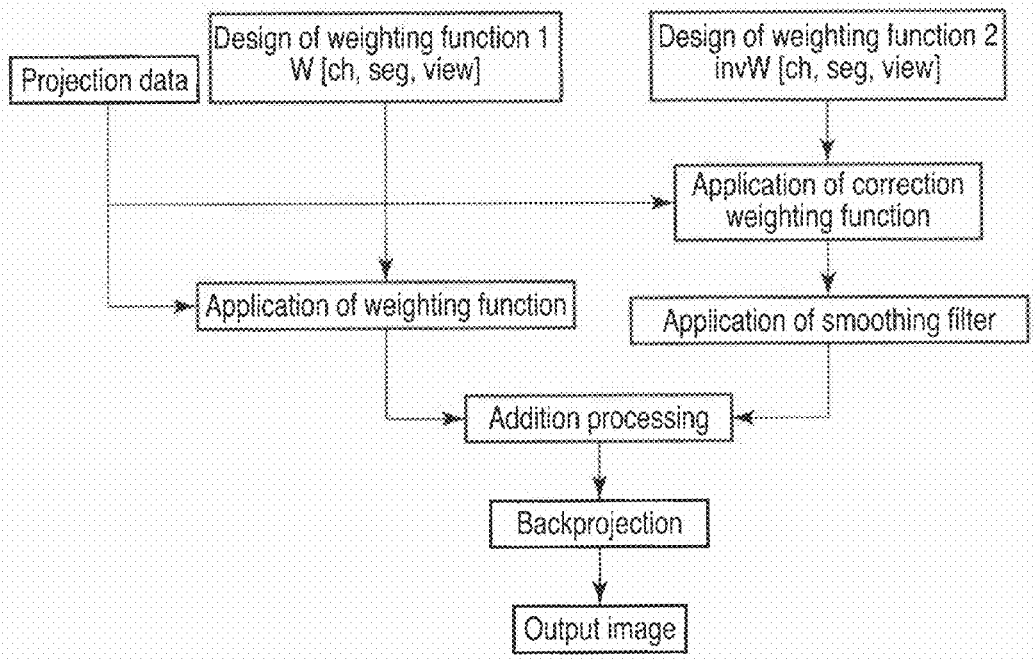
FIG. 9 is a flowchart showing a third image processing procedure in this embodiment.

The above two methods need to perform backprojection twice to obtain one image. However, performing addition at the projection data level can reduce the number of times of backprojection to one. As shown in FIG. 9, the method of designing the correction weighting function invW[ch, seg, view] is the same as that described above. This method differs from that described above in that smoothing is applied to data after the application of a correction weighting function. In this case, a smoothing filter is applied in the fan direction or the view direction. Thereafter, addition processing is performed. This addition method also considers a cone angle.

The following are the details of the above processing. Assume that the redundancy correction weighting function W[ch, seg, view] for half reconstruction uses the weight set by Parker et al. The correction weighting function invW[ch, seg, view] is defined by the following equation. Note that "*" represents convolution.

$$invW[ch,seg,view]=0.5-W[ch,seg,view]$$

When backprojection processing Proj[ch, seg, view] is multiplied by projection data, the respective intermediate data are given by $$W\_Proj[ch,seg,view]=W[ch,seg,view]*Proj[ch,seg,view]$$

$$invW\_Proj[ch,seg,view]=invW[ch,seg,view]*Proj[ch,seg,view]$$

Subsequently, low-pass filtering (smoothing filtering) is applied to the data. In this case, a Gaussian filter in the fan direction is used.

$$Filtered\_invW\_Proj[ch,seg,view]=invW\_Proj[ch,seg,view](X)Gaussian[ch]$$

In this case, if there are very many filter points, the processing speed increases. For this reason, it suffices to apply filtering to the projection data upon decreasing the number of data by folding them and unfold the data by interpolation or the like afterward. Finally, addition processing is performed. In this case, simple addition processing is performed without any consideration to a cone angle.

$$Processed\_Proj[ch,seg,view]=Filtered\_invW\_Proj[ch,seg,view]+W\_Proj[ch,seg,view]$$

Executing so-called FDK reconstruction proposed by Feldkamp et al. for processed projection data Processed_Proj [ch, seg, view] obtained by the above processing can maintain a time resolution equivalent to that in half reconstruction and reduce cone beam artifacts to a degree similar to that in full reconstruction. In this case, the obtained image quality is equivalent to that in full reconstruction, and the incompleteness of a circular orbit (cone beam problem) is not solved. However, applying the Line+Circle method proposed by Katsevich et al. to data obtained by the processing in this embodiment can achieve image quality similar to a complete solution.

Note that in the processing shown in FIGS. 7, 8, and 9, a useful effect can be obtained by changing the degree of correction in accordance with a cone angle. There is almost no need to correct an image obtained with a cone angle of 0°, i.e., at the central row (segment) of the detector. In contrast, strong correction is required for an image with a large cone beam, i.e., at a peripheral row of the detector. This correction degree adjustment technique (A) increases the weight W at the central row (seg) and decreases the weight at a peripheral row (seg). In addition, the correction weight invW is decreased at the central row (seg) and increased at a peripheral row (seg). Another correction degree adjustment technique (B) uses weighted addition in addition processing. In this technique, at the central row (seg), the weight for an object image is increased, and the weight for a correction image is decreased. In contrast, at a peripheral row (seg), the weight for an object image is decreased, and the weight for a correction image is increased. Typically, the correction degree adjustment technique (A) and the correction degree adjustment technique (B) are selectively used in accordance with a user instruction. However, it suffices to use both the correction degree adjustment technique (A) and the correction degree adjustment technique (B).

According to the present invention described above, half reconstruction requires full-rotation (one-rotation) data instead of half-rotation (180°+fan angle) data. As shown in FIG. 3, since smoothing is applied to data in an area other than the half-scanning area, there is no need to pay attention to the problem of noise.

That is, a sufficient correction effect can be obtained even if a certain dose is set for a time zone (the area indicated by light blue) corresponding to half scanning while the doses in other areas are suppressed to the degree that data are not impaired.

As shown in FIG. 4, when ECG-gated scanning/reconstruction is assumed to be used, applying the above concept makes it possible to apply a dose to full-rotation data in a phase designated in the following manner. This can suppress cone beam artifacts to a degree similar to that in full reconstruction while maintaining the half-scanning time resolution with respect to circular orbit scanning in cone beam CT.

Note that the present invention is not limited to the above embodiment, and constituent elements can be variously modified and embodied at the execution stage within the spirit and scope of the invention. Various inventions can be formed by proper combinations of a plurality of constituent elements disclosed in the above embodiments. For example, several constituent elements may be omitted from the all the constituent elements in each embodiment. In addition, constituent elements of the different embodiments may be combined as needed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus comprising:
a gantry which acquires projection data by scanning an object with cone beam X-rays;
a reconstruction processing unit which generates first volume data on the basis of a projection data set which covers an angle range of 180°+a fan angle and also generates second volume data on the basis of a projection data set which covers an angle range of 360°;
a correction data generating unit which generates correction data for reducing a cone beam artifact on the basis of a difference between the first volume data and the second volume data; and
a correction unit which corrects the first volume data on the basis of the correction data.

2. An X-ray computed tomography apparatus comprising:
a gantry which acquires projection data by scanning an object with cone beam X-rays;
a reconstruction processing unit which generates first volume data on the basis of a projection data set which covers an angle range of 180°+a fan angle and also generates second volume data on the basis of a projection data set which covers an angle range of 360°;
a correction data generating unit which generates correction data for reducing a cone beam artifact on the basis of the second volume data; and
a correction unit which corrects the first volume data on the basis of the correction data.

3. An X-ray computed tomography apparatus comprising:
a gantry which acquires projection data by scanning an object with cone beam X-rays;
a correction data generating unit which generates correction data for reducing a cone beam artifact on the basis of a projection data set which covers an angle range of 360°;
a correction unit which corrects a projection data set which covers an angle range of 180°+a fan angle on the basis of the correction data; and
a reconstruction processing unit which generates volume data on the basis of the corrected projection data set.

4. An X-ray computed tomography apparatus comprising:
a gantry which acquires projection data by scanning an object with cone beam X-rays;
a volume data generating unit which applies a first data redundancy correction weight to a first projection data set corresponding to a first angle range, generates first volume data on the basis of the first projection data set to which the weight is applied, applies a second data redundancy correction weight to a second projection data set corresponding to a second angle range wider than the first angle range, and generates second volume data on the basis of the second projection data set to which the weight is applied; and a correction unit which reduces a cone beam artifact by correcting the first volume data on the basis of a difference result between the first volume data and the second volume data.

5. The apparatus according to claim 4, wherein projection data to be processed by the volume data generating unit and the correction unit is data corresponding to not less than one rotation.

6. The apparatus according to claim 4, wherein the correction unit includes
a difference processing unit which generates third volume data by subtracting the first volume data and the second volume data from each other,
a smoothing unit which generates fourth volume data by applying smoothing to the third volume data, and
an addition unit which adds the fourth volume data to the first volume data.

7. The apparatus according to claim 6, wherein the smoothing unit applies two-dimensional filtering within an axial plane to the third volume data.

8. The apparatus according to claim 6, wherein the correction unit changes weights to be applied to the first volume data and the fourth volume data in accordance with a cone angle.

9. The apparatus according to claim 6, wherein the correction unit changes a degree of smoothing for the third volume data in accordance with a cone angle.

10. The apparatus according to claim 4, wherein the first data redundancy correction weight and the second data redundancy correction weight are generated to become 0.5 when data is accumulated with reference to a tube position into data corresponding to one rotation.

11. The apparatus according to claim 4, wherein the first angle range is 180°+a fan angle, and the second angle range is 360°.

12. An X-ray computed tomography apparatus comprising:
a gantry which acquires projection data by scanning an object with cone beam X-rays;
a volume data generating unit which applies a first data redundancy correction weight to a first projection data set corresponding to a first angle range, generates first volume data on the basis of the first projection data set to which the weight is applied, generates a third data redundancy correction weight by subtracting the first data redundancy correction weight from a second data redundancy correction weight corresponding to a second projection data set corresponding to a second angle range equal to or wider than the first angle range, applies the third data redundancy correction weight to the second projection data set, and generates second volume data on the basis of the second projection data set to which the weight is applied; and
a correction unit which reduces a cone beam artifact by correcting the first volume data on the basis of the second volume data.

13. The apparatus according to claim 12, wherein the third data redundancy correction weight is generated to become 0.5 when the first data redundancy correction weight and the second data redundancy correction weight are simply added, and data is accumulated with reference to a tube position into data corresponding to one rotation.

14. The apparatus according to claim 12, wherein projection data to be processed by the volume data generating unit and the correction unit is data corresponding to not less than one rotation.

15. The apparatus according to claim 12, further comprising a smoothing unit which applies smoothing to the second volume data to which the weight is applied.

16. The apparatus according to claim 15, wherein the smoothing unit applies two-dimensional filtering within an axial plane to the second volume data to which the two-dimensional filtering is applied.

17. An X-ray computed tomography apparatus comprising:
a gantry which acquires projection data by scanning an object with cone beam X-rays;
a correction unit which applies a first data redundancy correction weight to a first projection data set corresponding to a first angle range, generates a third data redundancy correction weight by subtracting the first data redundancy correction weight from a second data redundancy correction weight corresponding to a second projection data set corresponding a second angle range wider than the first angle range, applies the third data redundancy correction weight to the second projection data set, and corrects the first projection data set to which the weight is applied on the basis of the second projection data set to which the weight is applied; and
a volume data generating unit which generates volume data on the basis of the corrected first projection data set.

18. The apparatus according to claim 17, wherein the third data redundancy correction weight is generated to become 0.5 when the first data redundancy correction weight and the second data redundancy correction weight are simply added, and data is accumulated with reference to a tube position into data corresponding to one rotation.

19. The apparatus according to claim 17, wherein projection data to be processed by the correction unit and the volume data generating unit is data corresponding to not less than one rotation.

20. The apparatus according to claim 17, further comprising a smoothing unit which applies smoothing to the second projection data set to which the weight is applied.

21. The apparatus according to claim 20, wherein the smoothing unit applies filtering, in at least one of a fan direction and a view direction, to the second projection data set to which the weight is applied.

* * * * *